United States Patent
Steen

(10) Patent No.: US 9,576,390 B2
(45) Date of Patent: Feb. 21, 2017

(54) VISUALIZATION OF VOLUMETRIC ULTRASOUND IMAGES

(71) Applicant: General Electric Company, Schenectady, NY (US)

(72) Inventor: Erik Normann Steen, Moss (NO)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 150 days.

(21) Appl. No.: 14/508,433

(22) Filed: Oct. 7, 2014

(65) Prior Publication Data
US 2016/0098855 A1    Apr. 7, 2016

(51) Int. Cl.
| | | |
|---|---|---|
| G06T 15/08 | (2011.01) | |
| A61B 8/00 | (2006.01) | |
| G06T 15/80 | (2011.01) | |
| A61B 8/08 | (2006.01) | |

(52) U.S. Cl.
CPC ............ *G06T 15/08* (2013.01); *A61B 8/0841* (2013.01); *A61B 8/0866* (2013.01); *A61B 8/466* (2013.01); *A61B 8/467* (2013.01); *A61B 8/5207* (2013.01); *G06T 15/80* (2013.01); *A61B 8/4405* (2013.01); *A61B 8/465* (2013.01); *A61B 8/483* (2013.01); *G06T 2210/41* (2013.01)

(58) Field of Classification Search
None
See application file for complete search history.

(56) References Cited

U.S. PATENT DOCUMENTS

| | | | | |
|---|---|---|---|---|
| 2011/0255763 A1* | 10/2011 | Bogoni | ............... | G06T 19/00 382/131 |
| 2011/0270086 A1* | 11/2011 | Hoctor | ............. | A61B 8/4488 600/443 |
| 2013/0259351 A1* | 10/2013 | Wiemker, II | .......... | G06K 9/525 382/131 |
| 2013/0308849 A1* | 11/2013 | Fei | ........................ | G06T 7/0081 382/131 |
| 2014/0187948 A1* | 7/2014 | Gerard | ................ | A61B 8/5207 600/443 |
| 2015/0201907 A1* | 7/2015 | Stergiopoulos | ...... | A61B 8/5223 600/371 |

FOREIGN PATENT DOCUMENTS

WO    2006024973    3/2006

OTHER PUBLICATIONS

"Local Phase Coherence and the Perception of Blur", Wang and Simonecelli, Howard Hughes Medical Institute, Center for Neural Science and Courant Institute of Mathematical Sciences, 8 pages.

* cited by examiner

*Primary Examiner* — Ryan D McCulley
(74) *Attorney, Agent, or Firm* — McAndrews, Held & Malloy; Jacob Groethe; David Bates

(57) ABSTRACT

Various embodiments include systems and methods for adaptive visualization enhancement in volumetric ultrasound images. One or more structures may be determined or identified to be visually enhanced in the volumetric ultrasound images, and one or more visualization changes may be determined, for each of the one or more structures to be visually enhanced. Rendering adjustments required to achieve each of the one or more visualization changes, for each of the one or more structures to be visually enhanced, may then be determined; and the rendering adjustments may be applied during volume rendering of the volumetric ultrasound images.

17 Claims, 4 Drawing Sheets

Ultrasound Image without adaptive volumetric visualization enhancement

Ultrasound Image with adaptive volumetric visualization enhancement

Ultrasound image without adaptive volumetric visualization enhancement

Ultrasound image with adaptive volumetric visualization enhancement

VISUALIZATION OF VOLUMETRIC ULTRASOUND IMAGES

CLAIMS OF PRIORITY

Not Applicable

CROSS-REFERENCE TO RELATED APPLICATIONS/INCORPORATION BY REFERENCE

Not Applicable

FIELD OF THE INVENTION

Certain embodiments of the invention relate to ultrasound imaging. More specifically, certain embodiments of the invention relate to methods and systems for visualization of volumetric ultrasound images.

BACKGROUND OF THE INVENTION

Ultrasound imaging is a medical imaging technique for imaging organs and soft tissues in a human body. Ultrasound imaging uses real time, non-invasive high frequency sound waves to produce ultrasound images, which may be, for example, two-dimensional (2D) and/or three-dimensional (3D) images.

In some instances, different structures may be displayed in ultrasound images. For example, when imaging a particular organ, the ultrasound images may include structures associated the organ itself (e.g., walls, chambers, different tissue areas, etc.), structures associated with surrounding areas (e.g., other organs nearby), and/or structures associated with foreign objects that may be in proximity of the organ (e.g., catheters, etc.). The various structures may not very clearly distinguishable from one another. Users may have, however, varying levels of interest in the different structures displayed in the ultrasound images, such as based on the particular purpose for performing the ultrasound imaging. For example, the users may want to focus on existing foreign objects (e.g., catheters), such when using ultrasound images to assist in handling of these objections (e.g., monitoring and/or guiding movement of the catheters in patients' bodies). This may be difficult to do, however, when such objects are hard to distinguishing from surrounding tissue.

Further limitations and disadvantages of conventional and traditional approaches will become apparent to one of skill in the art, through comparison of such systems with some aspects of the present invention as set forth in the remainder of the present application with reference to the drawings.

BRIEF SUMMARY OF THE INVENTION

A system and/or method is provided for visualization of volumetric ultrasound images, substantially as shown in and/or described in connection with at least one of the figures, as set forth more completely in the claims.

These and other advantages, aspects and novel features of the present invention, as well as details of an illustrated embodiment thereof, will be more fully understood from the following description and drawings.

DETAILED DESCRIPTION OF THE INVENTION

Figure 1:
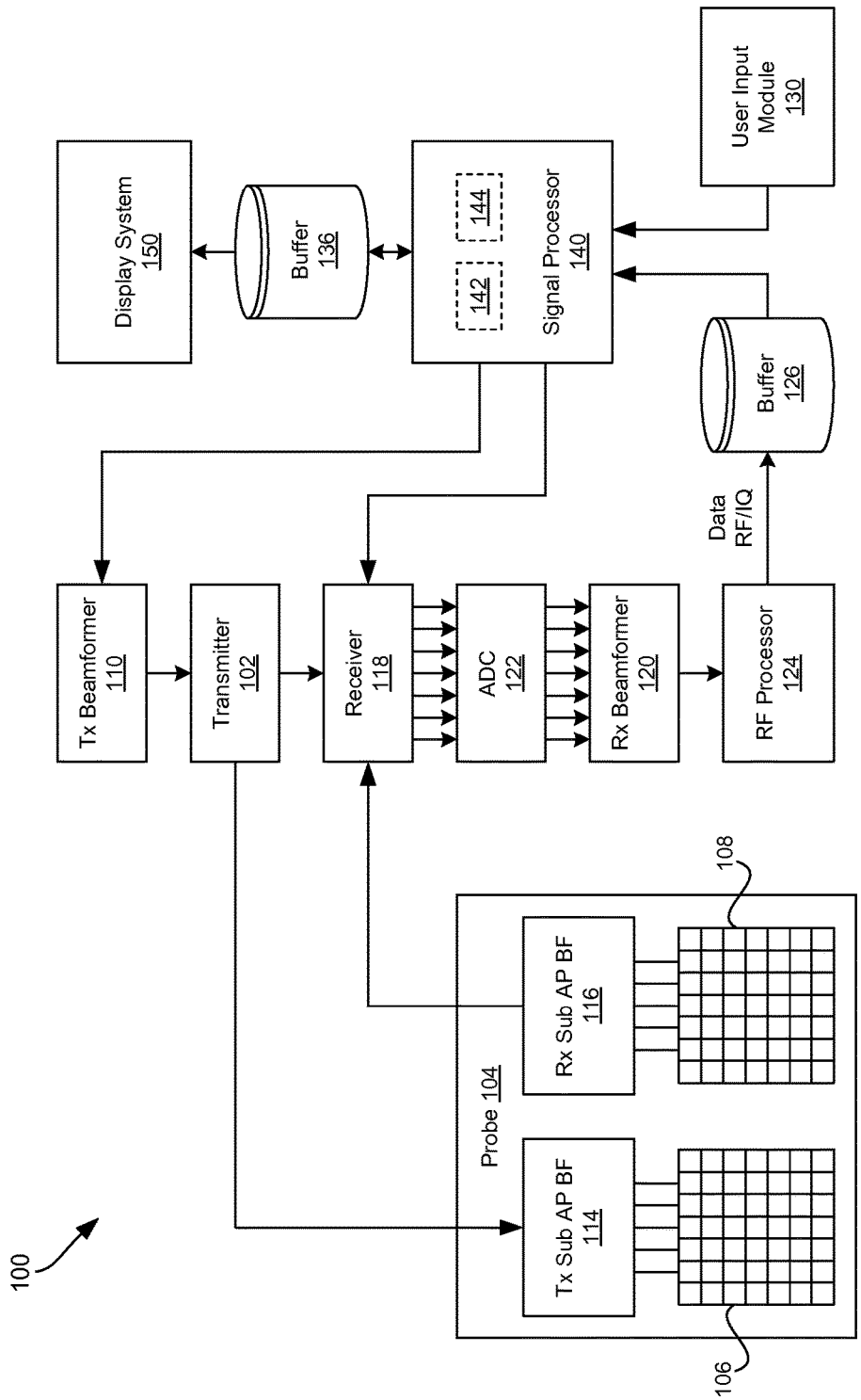
FIG. 1 is a block diagram illustrating an example ultrasound system that is operable to provide visualization of volumetric ultrasound images, in accordance with an embodiment of the invention.

Certain embodiments of the invention may be found in methods and systems for providing adaptive visualization (or enhancement thereof) in ultrasound images, particularly volumetric (e.g., 3D) ultrasound images. The visualization enhancement may be applied (in ultrasound systems, via suitable components thereof) to one or more volumetric ultrasound images, the data for which may be acquired in real-time. The application of visualization enhancement may comprise determining rendering adjustments required to achieve one or more visualization changes, for each of one or more structures to be visually enhanced in the one or more volumetric ultrasound images, and applying the rendering adjustments during rendering of the volumetric ultrasound images.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments of the present invention. The following detailed description is, therefore, not to be taken in a limiting sense, and the scope of the present invention is defined by the appended claims and their equivalents.

As used herein, an element or step recited in the singular and proceeded with the word "a" or "an" should be understood as not excluding plural of said elements or steps, unless such exclusion is explicitly stated. Furthermore, references to "an embodiment," "one embodiment," "a representative embodiment," "an example embodiment," "various embodiments," "certain embodiments," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

In addition, as used herein, the phrase "pixel" also includes embodiments of the present invention where the data is represented by a "voxel". Thus, both the terms "pixel" and "voxel" may be used interchangeably throughout this document.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode, CF-mode and/or submodes of CF such as TVI, Angio, B-flow, BMI, BMI_Angio, and in some cases also MM, CM, PW, TVD, CW where the "image" and/or "plane" includes a single beam or multiple beams.

Furthermore, the term processor or processing unit, as used herein, refers to any type of processing unit that can carry out the required calculations needed for the invention, such as single or multi-core: CPU, Graphics Board, DSP, FPGA, ASIC, or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing, including visualization enhancement, to form images may be performed, for example, in software, firmware, hardware, or a combination thereof. One implementation of an ultrasound system in accordance with various embodiments is illustrated in FIG. 1.

FIG. 1 is a block diagram illustrating an example ultrasound system that is operable to provide visualization of volumetric ultrasound images, in accordance with an embodiment of the invention. Shown in FIG. 1 is an ultrasound system 100.

The ultrasound system 100 comprises, for example, a transmitter 102, an ultrasound probe 104, a transmit beamformer 110, a receiver 118, a receive beamformer 120, a RF processor 124, a RF/IQ buffer 126, a user input module 130, a signal processor 140, an image buffer 136, and a display system 150.

The transmitter 102 may comprise suitable circuitry that may be operable to drive an ultrasound probe 104. The transmitter 102 and the ultrasound probe 104 may be implemented and/or configured for one dimensional (1D), two dimensional (2D), and/or three dimensional (3D) ultrasound scanning. In this regard, ultrasound probe 104 may comprise 1D or 2D array of piezoelectric elements. For example, as shown in FIG. 1, the ultrasound probe 104 may comprise a group of transmit transducer elements 106 and a group of receive transducer elements 108, that normally constitute the same elements. The transmitter 102 may be driven by the transmit beamformer 110. The transmit beamformer 110 may comprise suitable circuitry that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like).

The group of transmit transducer elements 106 can be activated to transmit ultrasonic signals. The ultrasonic signals may comprise, for example, pulse sequences that are fired repeatedly at a pulse repetition frequency (PRF), which may typically be in the kilohertz range. The pulse sequences may be focused at the same transmit focal position with the same transmit characteristics. A series of transmit firings focused at the same transmit focal position may be referred to as a "packet". The transmitted ultrasonic signals may be back-scattered from structures in the object of interest, like tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116 and are then communicated to a receiver 118.

The receiver 118 may comprise suitable circuitry that may be operable to receive and demodulate the signals from the probe transducer elements or receive sub-aperture beamformer 116. The demodulated analog signals may be communicated to one or more of the plurality of A/D converters (ADCs) 122.

Each plurality of A/D converters 122 may comprise suitable circuitry that may be operable to convert analog signals to corresponding digital signals. In this regard, the plurality of A/D converters 122 may be configured to convert demodulated analog signals from the receiver 118 to corresponding digital signals. The plurality of A/D converters 122 are disposed between the receiver 118 and the receive beamformer 120. Notwithstanding, the invention is not limited in this regard. Accordingly, in some embodiments of the invention, the plurality of A/D converters 122 may be integrated within the receiver 118.

The receive beamformer 120 may comprise suitable circuitry that may be operable to perform digital beamforming processing to, for example, sum the delayed channel signals received from the plurality of A/D converters 122 and output a beam summed signal. The resulting processed information may be converted back to corresponding RF signals. The corresponding output RF signals that are output from the receive beamformer 120 may be communicated to the RF processor 124. In accordance with some embodiments of the invention, the receiver 118, the plurality of A/D converters 122, and the beamformer 120 may be integrated into a single beamformer, which may be digital.

The RF processor 124 may comprise suitable circuitry that may be operable to demodulate the RF signals. In accordance with an embodiment of the invention, the RF processor 124 may comprise a complex demodulator (not shown) that is operable to demodulate the RF signals to form In-phase and quadrature (IQ) data pairs (e.g., B-mode data pairs) which may be representative of the corresponding echo signals. The RF or IQ signal data may then be communicated to an RF/IQ buffer 126.

The RF/IQ buffer 126 may comprise suitable circuitry that may be operable to provide temporary storage of output of the RF processor 124—e.g., the RF or IQ signal data, which is generated by the RF processor 124.

The user input module 130 may comprise suitable circuitry that may be operable to enable obtaining or providing input to the ultrasound system 100, for use in operations thereof. For example, the user input module 130 may be used to input patient data, surgical instrument data, scan parameters, settings, configuration parameters, change scan mode, and the like. In an example embodiment of the invention, the user input module 130 may be operable to configure, manage and/or control operation of one or more components and/or modules in the ultrasound system 100. In this regard, the user input module 130 may be operable to configure, manage and/or control operation of transmitter 102, the ultrasound probe 104, the transmit beamformer 110, the receiver 118, the receive beamformer 120, the RF processor 124, the RF/IQ buffer 126, the user input module 130, the signal processor 140, the image buffer 136, and/or the display system 150.

The signal processor 140 may comprise suitable circuitry that may be operable to process the ultrasound scan data (e.g., the RF and/or IQ signal data) and/or to generate corresponding ultrasound images, for presentation on a display system 150. The signal processor 140 is operable to perform one or more processing operations according to a plurality of selectable ultrasound modalities on the acquired ultrasound scan data. In some instances, the signal processor 140 may be operable to perform compounding, motion tracking, and/or speckle tracking. Acquired ultrasound scan data may be processed in real-time—e.g., during a B-mode scanning session, as the B-mode echo signals are received. Additionally or alternatively, the ultrasound scan data may be stored temporarily in the RF/IQ buffer 126 during a scanning session and processed in less than real-time in a live or off-line operation.

In operation, the ultrasound system 100 may be used in generating ultrasonic images, including two-dimensional (2D) and/or three-dimensional (3D) images. In this regard, the ultrasound system 100 may be operable to continuously acquire ultrasound scan data at a particular frame rate, which may be suitable for the imaging situation in question. For example, frame rates may range from 20-70 but may be lower or higher. The acquired ultrasound scan data may be displayed on the display system 150 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several seconds' worth of frames of ultrasound scan data. The frames of ultrasound scan data are stored in a manner to facilitate retrieval thereof according to its order or time of acquisition. The image buffer 136 may be embodied as any known data storage medium.

In some instances, the ultrasound system 100 may be configured to support grayscale and color based operations. For example, the signal processor 140 may be operable to perform grayscale B-mode processing and/or color processing. The grayscale B-mode processing may comprise processing B-mode RF signal data or IQ data pairs. For example, the grayscale B-mode processing may enable forming an envelope of the beam-summed receive signal by computing the quantity $(I^2+Q^2)^{1/2}$. The envelope can undergo additional B-mode processing, such as logarithmic compression to form the display data. The display data may be converted to X-Y format for video display. The scan-converted frames can be mapped to grayscale for display. The B-mode frames that are provided to the image buffer 136 and/or the display system 150. The color processing may comprise processing color based RF signal data or IQ data pairs to form frames to overlay on B-mode frames that are provided to the image buffer 136 and/or the display system 150. The grayscale and/or color processing may be adaptively adjusted based on user input—e.g., a selection from the user input module 130, for example, for enhance of grayscale and/or color of particular area.

In some instances, ultrasound images may comprise various and different structures. For example, during B-mode ultrasound imaging, when imaging a particular part or organ of a patient, the generated ultrasound images may include structures associated the part or organ itself (e.g., walls, chambers, different tissue areas, etc.), structures associated with surrounding areas (e.g., other organs nearby, etc.). Further, in some instances the ultrasound images may comprise structures associated with foreign objects that may be in proximity of the part or organ. Examples of foreign objects may comprise catheters and the like, which may be inserted into the patient's body (e.g., before or during the ultrasound imaging). In some instances, the various structures displayed in ultrasound images may not very clearly distinguishable from one another. Users may have, however, varying levels of interest in the different structures displayed in the ultrasound images, such as based on the particular purpose for performing the ultrasound imaging. For example, the users may want to focus on existing foreign objects (e.g., catheters), such when using ultrasound images to assist in handling of these objections (e.g., monitoring and/or guiding movement of the catheters in patients' bodies). This may be difficult to do, however, when such objects are hard to distinguishing from surrounding tissues. This may be particularly the case with B-mode volumetric ultrasound images (e.g., 3D ultrasound images). In this regard, it may be particularly hard to visually distinguish different structures in the volumetric B-mode images, and to particularly do so three-dimensionally in effective manner—e.g., to display various structures in a volume in a way that visually emphasizes certain structures from other structures.

Accordingly, in various embodiments according to the present invention, volumetric ultrasound images, particularly volumetric B-mode ultrasound images, may be enhanced to allow for improved visualization of the various structures therein. This may be particularly desirable in certain use scenarios. Enhanced volumetric visualization may be desirable, for example, where particular structures in the volumetric images need to be made particular distinctive in relation to and/or distinguishable from other (particular surrounding) structures in the volumetric images. For example, volumetric imaging may work well in cases where there are no man-made objects (e.g., catheters) present in the volume. However, introducing objects may cause issues. As a user (e.g., interventionalist) inserts, for example, a catheter it would be desirable to show the catheter in a different way than its surroundings (e.g., shinier, with a non-saturated color). Another use scenario is visually discriminating calcified valves from other structures. Further, in another use scenario only very prominent structures may be made shiny while less prominent structures not so shiny—e.g., to reduce impact of noise.

In certain example embodiments according to the present invention, enhancing visualization in volumetric ultrasound images may be achieved by generating and/or processing the ultrasound images to visualize particular types of structures in a 3D ultrasound data, such as using different display parameters. This may comprise different grayscale and/or color based adjustments. For example, certain structures may be visualized using gradient shading with strong specular highlights (creating shiny surfaces), while other structures may be visualized with only diffuse shading. Further, in some instance, coloring of different structures may be varied. For example, in an interventional setting, a distinct visual difference may be created between a prominent feature such as a catheter and less pronounced features (e.g., surrounding tissue). The visualization enhancement may not depend on any previous explicit image segmentation. Rather, local image properties may be based on local properties, such as local image coherence, which may be derived at multiple scales, and which may then be used to control the adjustments (e.g., amount of diffuse shading, specular shading, and/or color) for the voxels in the volumetric images. For example, the wavelets may be used in measuring local image coherence, which may then be used to control amount of (or adjustment to) shading and/or coloring. Accordingly, the visualization enhancement scheme may not attempt to explicitly classify voxels as belonging (or not) to certain structures. Rather, the visualization enhancement scheme may be a simple fuzzy classification scheme to visually discriminate different structures in the volume For example, the ultrasound system 100 may be configured to support visualization enhancement of volumetric ultrasound images, such as based on use of adaptive shading and coloring adjustment. In this regard, the ultrasound system 100 may be configured to acquire volumetric ultrasound dataset (e.g., in real time), which may then be used to generate corresponding 3D ultrasound images that may be displayed (e.g., via the display system 150), such as using volume rendering. For example, the signal processor 140 may comprise a volume rendering module 142, which may comprise suitable circuitry for determining and/or applying volume rendering and/or adjustments thereof. The volume rendering may comprise use and/or application of gradient shading and potentially soft shadowing techniques. For example, amount of diffuse shading and/or the amount of specular shading may be adjusted per voxel. Further, the voxel color may be adjusted.

The volume rendering related adjustments may be based on image properties. For example, the signal processor 140 may comprise an image analyzer module 144, which may comprise suitable circuitry for analyzing images in order to obtain or generate data that may be pertinent to determining volume rendering related adjustments. In particular, the image analyzer module 144 may be configured to analyze images in particular manner based on the type of volume rendering related adjustments applied in the system. For example, the adjustments of the shading and/or color related parameters may be based on local image properties, for instance based on, for example, local image coherence. Thus, the image analyzer module 144 may be configured to perform local image coherence based analysis.

In an example implementation, the image analysis (and determining adjustment based thereon) may be based on wavelet and measurements thereof. In this regard, analyzing images (e.g., via image analyzer module 144) may comprise creating a multi-scale (e.g., wavelet) representation corresponding to the analyzed images. For example, a simple dyadic wavelet transform (e.g., Haar wavelet) may be used to create a multi-scale representation of the volumetric dataset acquired in real time. Voxels corresponding to particular structure (or portion thereof) may meet particular characterization in the multi-scale representation, and as such, only voxels meeting such characterization would subject the adjustments deemed necessary to achieve the desirable (or required) visualization. For example, in some instances where the structure to be visually enhanced may be a particular object (e.g., a catheter), with the particular desired enhancement may be to appear more "shiny" than other structures, a multi-scale representation of the volumetric dataset may be created (e.g., using simple Haar wavelet), with the multi-scale representation being used when analyzing the image to identify voxels that belong to the structure (e.g., the catheter), or particular part thereof (e.g., surface of the catheter). For example, such voxels may be characterized as having a strong gradient magnitude across multiple scales and having consistent normal direction across multiple scales. In the wavelet domain this may correspond to having coherent wavelet coefficients in H, V, and HV bands across several scales.

To further discriminate the desired structure (e.g., the catheter) from other structures, additional measures may be used and/or applied. For example, to discriminate the catheter from other structures, measures of curvature at a coarse scale may also be applied, since the catheter's surface would be convex in one dimension while straight in another. Other measurements such as second (2nd) order derivatives may also be used. By combining different measurements the likelihood of emphasizing mainly the desired structure (e.g., the catheter) may increase. Accordingly, rather than needing to explicitly classify each voxel as belonging (or not) to a certain structure, the visualization enhancement scheme may implemented based on fuzzy classification of voxels to visually discriminate different structures in the volume.

Determining the structure(s), and/or the particular parts or elements thereof, to be visually enhanced, and/or the particular (desired) adjustments to be applied may be based on real-time user selection (e.g. using suitable control or user input means, such as the user input module 130), and/or based on pre-configured or pre-programmed settings, selections, and/or selection criteria. For example, as noted in the example use scenario described above, the structure to be visually enhanced may be man-made objects (such as catheters), with the particular part/element to be enhanced being the surface, and particular desired enhancement being that the catheter's surface appearing more "shiny" than other structures; with all these being specified by the user (e.g., interventionalist) in real-time, using suitable user control in the ultrasound system 100 (not shown).

Figure 2:
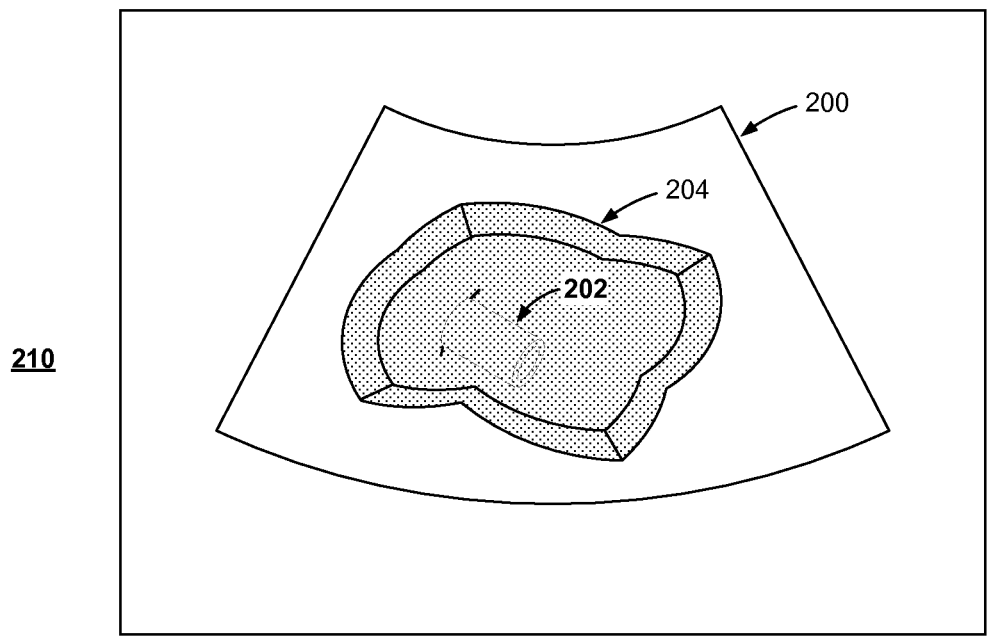
FIG. 2 illustrates example use of adaptive visualization in a volumetric ultrasound image, in accordance with an embodiment of the invention.
Figure 2:
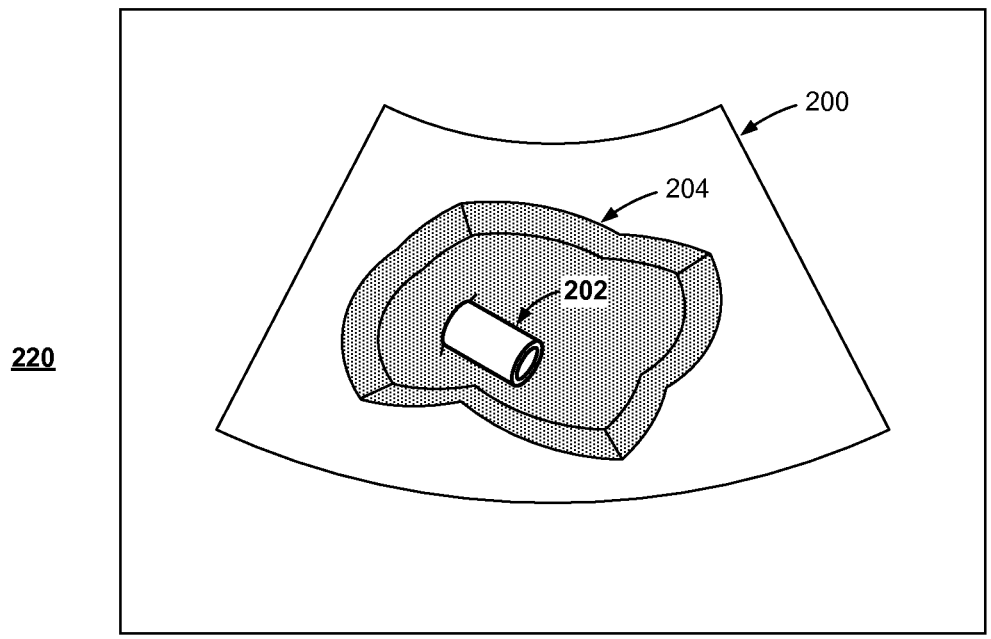

FIG. 2 illustrates example use of adaptive visualization in a volumetric ultrasound image, in accordance with an embodiment of the invention. Shown in FIG. 2 are ultrasound image frames 210 and 220, each of which comprising an ultrasound image 200. In particular, the ultrasound image frames 210 and 220 may correspond to use (or not) of adaptive visualization enhancement of volumetric ultrasound images in an ultrasound system, such as the ultrasound system 100 of FIG. 1.

The ultrasound image 200 may be a volumetric ultrasound image—that is an ultrasound image displayed using volume rendering, to provide 2D perception. The ultrasound image 200 may comprise a plurality of different structures. For example, as shown in FIG. 2, the ultrasound image 200 may comprise an object (e.g., catheter) 202 inserted (or being inserted) within an organ or tissue area 204.

The ultrasound image frame 210 may correspond to displaying the ultrasound image 200 without visualization enhancement. As a result, as shown in frame 210, the object (e.g., catheter) 202 may be hard to distinguish from the surrounding organ or tissue area 204.

The ultrasound image frame 220 may correspond to displaying the same ultrasound image 200 but with adaptive visualization enhancement. In this regard, the volume rendering may be applied such that it may incorporate adjustments for visually enhancing particular elements of the image. The user may select (e.g., using user controls) to visually enhance man-made objects (e.g., the object 202) in relation to surrounding tissue. The ultrasound system may analyze the images (e.g., using local coherence based analysis) to determine suitable visualization enhancement for voxels corresponding to the object 202. Further, in some instances, rendering of the surrounding area (e.g., tissue or organ 204) may also be adjusted to further visually enhance the intended structure (the object 202), such as to increase the contrast between the two structures. As a result, as shown in frame 220, the object (e.g., catheter) 202 may clearly distinguishable from the surrounding organ or tissue area 204.

Figure 3:
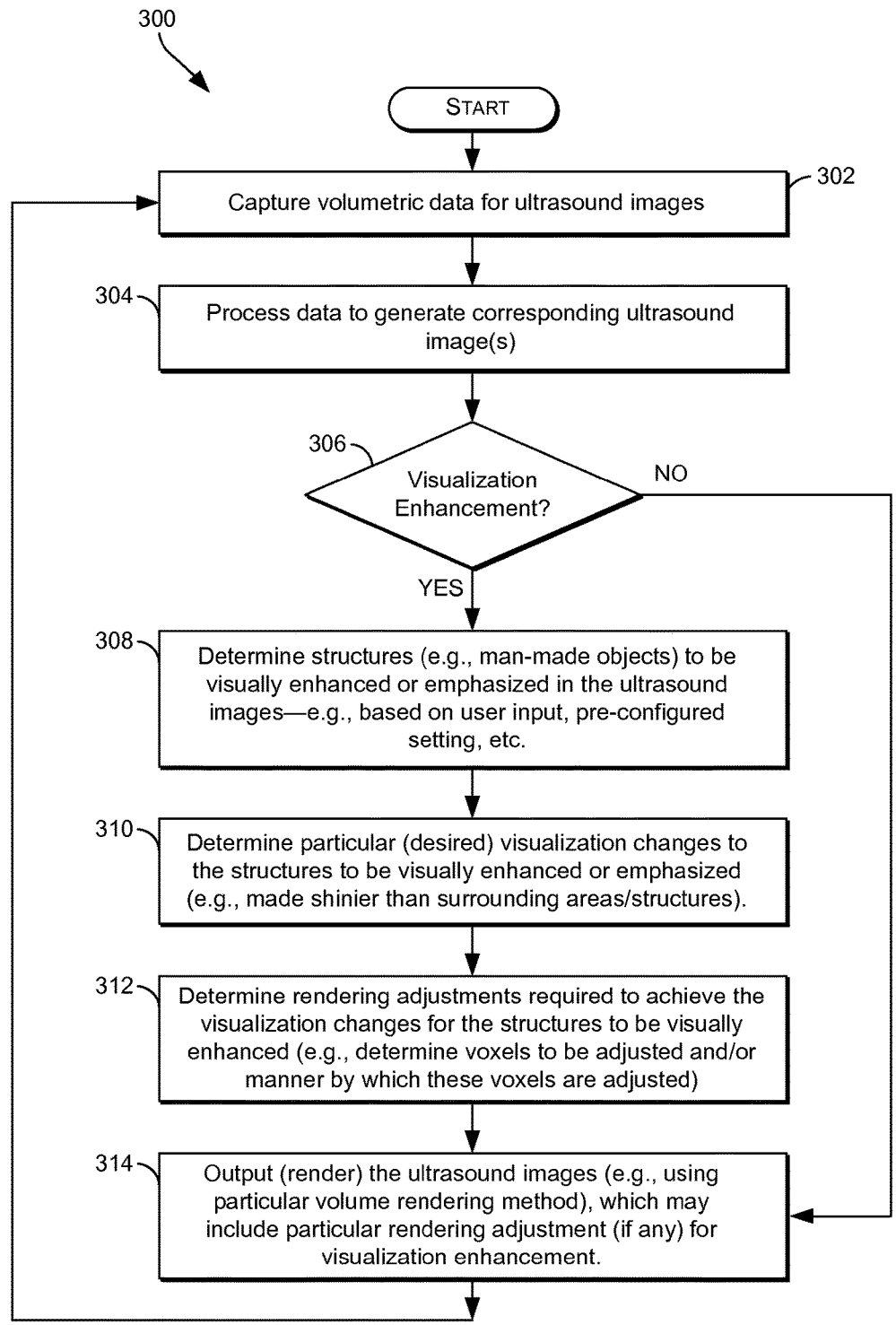
FIG. 3 is a flow chart illustrating example steps that may be utilized for providing adaptive visualization in volumetric ultrasound images, in accordance with an embodiment of the invention.

FIG. 3 is a flow chart illustrating example steps that may be utilized for providing adaptive visualization in volumetric ultrasound images, in accordance with an embodiment of the invention. Shown in FIG. 3 is a flow chart 300, which comprises a plurality of example steps, corresponding to an example method. The technical effect of the method corresponding to flow chart 300 is providing adaptive visualization in volumetric ultrasound images by an ultrasound system (e.g., the ultrasound system 100, shown in FIG. 1). For example, the example steps of the method corresponding to flow chart 300 may be executed and/or performed by the various components of the ultrasound system 100, such as the processor 130, the volume rendering module 142, the image analyzer module 144, and the display system 150.

It should be understood, however, that certain embodiments of the present invention may omit one or more of the steps, and/or perform the steps in a different order than the order listed, and/or combine certain of the steps discussed below. For example, some steps may not be performed in certain embodiments of the present invention. As a further example, certain steps may be performed in a different temporal order, including simultaneously, than listed below.

In step 302, data corresponding to a sequence of ultrasound images may be obtained, such as using an ultrasound system (e.g., the ultrasound system 100 of FIG. 1). For example, the ultrasound images may be volumetric (3D) images, and as such the data may comprise volumetric data—that is data that may enable providing volume rendering.

In step 304, ultrasound images may be generated, such as based on processing of the data obtained or acquired in the previous step (step 302). The processing may comprise grayscale B-mode processing and/or color processing. Further, in some instances, the processing may comprise additional functions and/or adjustments, some of which being performed conditionally (e.g., when needed), to achieve particular desired outcome (e.g., visualization enhancement).

For example, in step 306, it may be determined whether to visually enhance the would-be displayed images. In this regard, visualization enhancement may be triggered in response to system pre-configuration, user input/commands, etc. In instances where no visualization enhancement is triggered, the process may jump to step 314; otherwise the process may proceed to step 308.

In step 308, particular structures (e.g., man-made objects) to be visually enhanced or emphasized in the ultrasound images may be determined or identified—e.g., based on user input (such as being identified or marked in previous images using user controls, touch-screen, etc.), pre-configured setting, etc.

In step 310, particular (desired) visualization changes, to the structures to be visually enhanced or emphasized, may be determined or identified (e.g., made shinier than surrounding areas/structures).

In step 312, rendering adjustments required to achieve the visualization changes for the structures to be visually enhanced may be determined. For example, the voxels to be adjusted may be identified, and for each of the identified voxels, the manner by which these voxels are adjusted may be determined. The voxels may correspond to the structures to be visually enhanced and/or voxels corresponding to surrounding area. The adjustments may comprise changes needed to adjust amount of shading and/or coloring in each of the voxels, for example.

In step 314, the ultrasound image(s), which may be visually enhanced (by adjusting particular voxels), may be displayed. The displaying of ultrasound may comprise use of volume rendering (to provide the volumetric effect). The process may then loop back to step 302, to continue handling additional/subsequently-acquired data (or may terminate if the operation of the ultrasound system is ceased).

Figure 4:
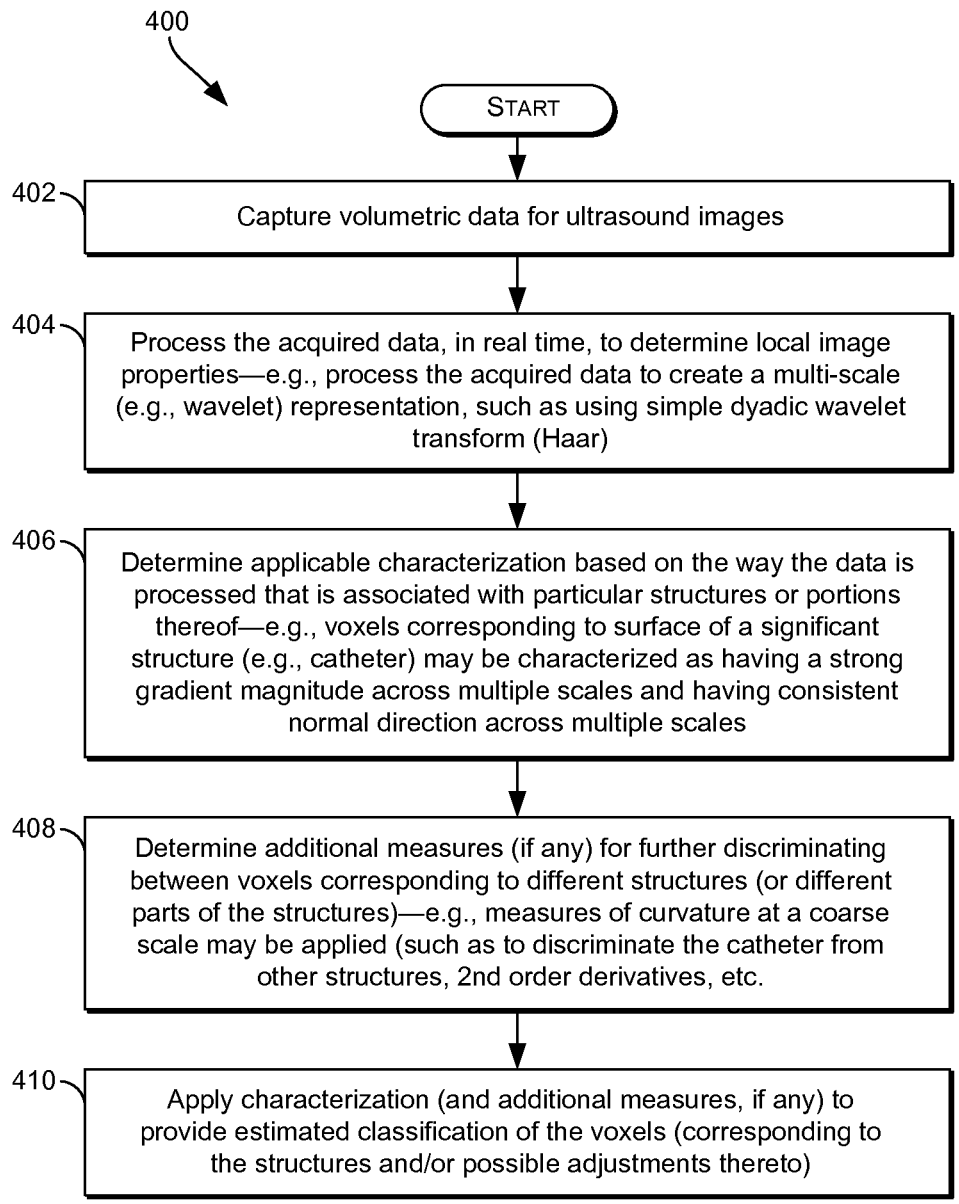
FIG. 4 is a flow chart illustrating example steps that may be utilized for processing ultrasound images during application of adaptive visualization enhancement, in accordance with an embodiment of the invention.

FIG. 4 is a flow chart illustrating example steps that may be utilized for processing ultrasound images during application of adaptive visualization enhancement, in accordance with an embodiment of the invention. Shown in FIG. 4 is a flow chart 400, which comprises a plurality of example steps, corresponding to an example method. The technical effect of the method corresponding to flow chart 400 is processing ultrasound images, particularly in conjunction with and/or in support of adaptive visualization in volumetric ultrasound images, in an ultrasound system (e.g., the ultrasound system 100, shown in FIG. 1). For example, the example steps of the method corresponding to flow chart 400 may be executed and/or performed by the various components of the ultrasound system 100, such as the processor 130 and the image analyzer module 144.

It should be understood, however, that certain embodiments of the present invention may omit one or more of the steps, and/or perform the steps in a different order than the order listed, and/or combine certain of the steps discussed below. For example, some steps may not be performed in certain embodiments of the present invention. As a further example, certain steps may be performed in a different temporal order, including simultaneously, than listed below.

In step 402, data corresponding to a sequence of ultrasound images may be obtained, such as using an ultrasound system (e.g., the ultrasound system 100 of FIG. 1). For example, the ultrasound images may be volumetric (3D) images, and as such the data may comprise volumetric data—that is data that may enable providing volume rendering.

In step 404, the acquired data may be processed, in real time, such as to determine local image properties. For example, the acquired data may be processed to create a multi-scale (e.g., wavelet) representation, such as using simple dyadic wavelet transform (Haar).

In step 406, an applicable characterization, associated with particular structures or portions thereof, may be determined, based on the method by which the data is process. For example, with wavelet (e.g., local coherence) based processing, voxels corresponding to surface of a significant structure (e.g., catheter) may be characterized as having a strong gradient magnitude across multiple scales and having consistent normal direction across multiple scales.

In step 408, additional measures (if any) may be determined for further discriminating between voxels corresponding to different structures (or different parts of the structures). For example, measures of curvature at a coarse scale may be applied (such as to discriminate the catheter from other structures, 2nd order derivatives, etc.

In step 410, the main characterization (and additional measures, if any) may be applied to provide estimated classification of the voxels (corresponding to the structures and/or possible adjustments thereto).

Aspects of the present invention have the technical effect of providing adaptive visualization in volumetric ultrasound images in computationally efficient manner. In particular, visualization of particular structures in volumetric (3D) ultrasound images may be enhanced, in real time, to help improve understanding of 3D images, without requiring extensive user interactions. In accordance with various example embodiments of the invention, voxels that may be adjusted for enhanced visualization may be identified in data (e.g., volumetric data) corresponding to the volumetric ultrasound images; and particular adjustments (e.g., shading and/or coloring adjustments) may be determined to the identified voxels (or subsets thereof), with these adjustments being effectuated during rendering (e.g., volume rendering) of the volumetric ultrasound images. The voxels may be identified based on analysis of the images (or of the data corresponding to the image). In particular, the analysis may enable estimating groups of voxels corresponding to particular structures (or parts thereof) in the images.

As utilized herein the term "circuitry" refers to physical electronic components (e.g., hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "example" means serving as a non-limiting example, instance, or illustration. As utilized herein, the terms "for example" and "e.g.," set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled, or not enabled, by some user-configurable setting.

Other embodiments of the invention may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for providing sequential needle recalibration by correlating a sequence of calibration data for a tracking system to a plurality of corresponding ultrasound probe positions.

Accordingly, the present invention may be realized in hardware, software, or a combination of hardware and software. The present invention may be realized in a centralized fashion in at least one computer system, or in a distributed fashion where different elements are spread across several interconnected computer systems. Any kind of computer system or other apparatus adapted for carrying out the methods described herein is suited. A typical combination of hardware and software may be a general-purpose computer system with a computer program that, when being loaded and executed, controls the computer system such that it carries out the methods described herein.

The present invention may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

What is claimed is:

1. A method, comprising:
applying, by a processor of an ultrasound system, visualization enhancement to one or more volumetric ultrasound images, the visualization enhancement comprising:
determining one or more structures to be visually enhanced in the volumetric ultrasound images;
determining one or more visualization changes, for each of the one or more structures to be visually enhanced;
processing the volumetric ultrasound images to determine local image properties that control one or more characteristics of at least a portion of each volumetric ultrasound image, wherein the local image properties comprise local image coherence that is characterized as having one or more of:
a strong gradient magnitude across multiple scales,
consistent normal direction across multiple scales, and
coherent wavelet coefficients in multiple bands across multiple scales;
determining rendering adjustments required to achieve each of the one or more visualization changes, for each of the one or more structures to be visually enhanced, wherein the rendering adjustments are determined, at least in part, based on the processing of the volumetric ultrasound images, wherein the local image coherence is used to control amount of one or more of diffuse shading, specular shading, and color of voxels in the volumetric ultrasound images; and
applying the rendering adjustments during volume rendering of the volumetric ultrasound images.

2. The method of claim 1, comprising processing the volumetric ultrasound images to estimate portions thereof corresponding to the one or more structures to be visually enhanced.

3. The method of claim 1, wherein the rendering adjustments comprise grayscale and/or color related adjustments.

4. The method of claim 1, comprising determining the one or more structures, and/or the one or more visualization changes for each of the one or more structures to be visually enhanced, based on user input.

5. The method of claim 1, comprising determining the one or more structures, and/or the one or more visualization changes for each of the one or more structures to be visually enhanced, based on pre-configured or pre-programmed settings, selections, and/or selection criteria.

6. The method of claim 1, wherein the one or more visualization changes for at least one structure to be visually enhanced comprise making the at least one structure shinier relative to surrounding structures by applying gradient shading with specular highlights.

7. A system, comprising:
an ultrasound device comprising a processor that is operable to apply visualization enhancement to one or more volumetric ultrasound images, the visualization enhancement comprising:
  determining one or more structures to be visually enhanced in the volumetric ultrasound images;
  determining one or more visualization changes, for each of the one or more structures to be visually enhanced;
  processing the volumetric ultrasound images to determine local image properties that control one or more characteristics of at least a portion of each volumetric ultrasound image, wherein the local image properties comprise local image coherence that is characterized as having one or more of:
    a strong gradient magnitude across multiple scales,
    consistent normal direction across multiple scales, and
    coherent wavelet coefficients in multiple bands across multiple scales;
  determining rendering adjustments required to achieve each of the one or more visualization changes, for each of the one or more structures to be visually enhanced, wherein the rendering adjustments are determined, at least in part, based on the processing of the volumetric ultrasound images, wherein the local image coherence is used to control amount of one or more of diffuse shading, specular shading, and color of voxels in the volumetric ultrasound images; and
  applying the rendering adjustments during volume rendering of the volumetric ultrasound images.

8. The system of claim 7, wherein the processor is operable to process the volumetric ultrasound images to estimate portions thereof corresponding to the one or more structures to be visually enhanced.

9. The system of claim 7, wherein the rendering adjustments to the volumetric ultrasound images comprise grayscale and/or color related adjustments.

10. The system of claim 7, wherein the one or more structures, and/or the one or more visualization changes for each of the one or more structures to be visually enhanced, are determined based on user input.

11. The system of claim 7, wherein the one or more structures, and/or the one or more visualization changes for each of the one or more structures to be visually enhanced, are determined based on pre-configured or pre-programmed settings, selections, and/or selection criteria.

12. The system of claim 7, wherein the one or more visualization changes for at least one structure to be visually enhanced comprise making the at least one structure shinier relative to surrounding structures by applying gradient shading with specular highlights.

13. A non-transitory computer readable medium having stored thereon, a computer program having at least one code section, the at least one code section being executable by a machine for causing the machine to apply visualization enhancement to one or more volumetric ultrasound images by perform steps comprising:
  determining one or more structures to be visually enhanced in the volumetric ultrasound images;
  determining one or more visualization changes, for each of the one or more structures to be visually enhanced;
  processing the volumetric ultrasound images to determine local image properties that control one or more characteristics of at least a portion of each volumetric ultrasound image, wherein the local image properties comprise local image coherence that is characterized as having one or more of:
    a strong gradient magnitude across multiple scales,
    consistent normal direction across multiple scales, and
    coherent wavelet coefficients in multiple bands across multiple scales;
  determining rendering adjustments required to achieve each of the one or more visualization changes, for each of the one or more structures to be visually enhanced, wherein the rendering adjustments are determined, at least in part, based on the processing of the volumetric ultrasound images, wherein the local image coherence is used to control amount of one or more of diffuse shading, specular shading, and color of voxels in the volumetric ultrasound images; and
  applying the rendering adjustments during volume rendering of the volumetric ultrasound images.

14. The non-transitory computer readable medium of claim 13, comprising processing the volumetric ultrasound images to estimate portions thereof corresponding to the one or more structures to be visually enhanced.

15. The non-transitory computer readable medium of claim 13, wherein the rendering adjustments to the volumetric ultrasound images comprise grayscale and/or color related adjustments.

16. The non-transitory computer readable medium of claim 13, comprising determining the one or more structures, and/or the one or more visualization changes for each of the one or more structures to be visually enhanced, based on user input.

17. The non-transitory computer readable medium of claim 13, comprising determining the one or more structures, and/or the one or more visualization changes for each of the one or more structures to be visually enhanced, based on pre-configured or pre-programmed settings, selections, and/or selection criteria.

* * * * *